United States Patent [19]
Darby

[11] Patent Number: 5,940,992
[45] Date of Patent: Aug. 24, 1999

[54] SURGICAL SHOE FOR AVOIDING HEEL STRIKE AND FOR REDUCING WEIGHT BEARING FROM THE HEEL OF A FOOT

[75] Inventor: H. Darrel Darby, Huntington, W. Va.

[73] Assignee: Darco International, Inc., Huntington, W. Va.

[21] Appl. No.: 09/039,334

[22] Filed: Mar. 16, 1998

[51] Int. Cl.$^6$ ....................................................... A43B 3/00
[52] U.S. Cl. ................................. 36/110; 36/103; 36/76 R
[58] Field of Search .............................. 36/110, 103, 140, 36/142, 143, 144, 76 R

[56] References Cited

U.S. PATENT DOCUMENTS

| | | |
|---|---|---|
| 3,061,949 | 11/1962 | Rosenbaum . |
| 3,633,573 | 1/1972 | Lipson . |
| 4,677,767 | 7/1987 | Darby . |
| 4,726,127 | 2/1988 | Barouk . |
| 5,088,481 | 2/1992 | Darby . |
| 5,138,777 | 8/1992 | Darby . |
| 5,491,909 | 2/1996 | Darby . |
| 5,617,651 | 4/1997 | Prahl . |
| 5,694,706 | 12/1997 | Penka . |

FOREIGN PATENT DOCUMENTS 2932855   2/1981   Germany .
2136267   9/1984   United Kingdom .

OTHER PUBLICATIONS ipos® Orthopedics Industry advertisement of ipos Heel Relief Orthosis medical shoe, publication date unknown.

Primary Examiner—Ted Kavanaugh
Attorney, Agent, or Firm—Sughrue, Mion, Zinn, Macpeak & Seas, PLLC

[57] ABSTRACT

A wedge outsole of generally triangular shaped configuration as viewed from a side thereof is integrated to an insole and shoe upper of a post-operative surgical shoe. The outsole has a flat top surface integrated to the bottom surface of the insole, with the outsole having a thickest portion of a wedge located under a part of the foot just in front of the heel, preferably centered, with the proximal portion of the arch of the user's foot. An integral, substantially thinner portion extends rearwardly from and underlying the heel of the foot from the thickest portion, thereby defining a rearwardly extending recess. The shoe insole comprises a frontal section overlying the outsole from the thickest portion of the tapering outsole to the toe end of the shoe of an impact absorbing material of medium density and a rear section underlying the heel of the foot such as a soft foam or gel to cradle and protect the heel, thereby relieving the shoe of a weight bearing heel portion and facilitating ambulation of the foot about a rocker edge remote from the heel to avoid heel strike during ambulation.

10 Claims, 5 Drawing Sheets

SURGICAL SHOE FOR AVOIDING HEEL STRIKE AND FOR REDUCING WEIGHT BEARING FROM THE HEEL OF A FOOT

FIELD OF THE INVENTION

The present invention relates to post-operative surgical shoe for comfortably supporting a post-operative or otherwise traumatized patient's heel, and more particularly to such surgical shoe having a molded sole especially configured to prevent heel strike and to force weight on the initial impact of the foot with the ground to an area of the foot anterior to the medial tuberosity.

BACKGROUND OF THE INVENTION

A number of foot conditions affect primarily the rear foot or heel portion of the foot. Post-operative surgical shoes are designed in a number of ways including a dominant type that removes the weight from the forefoot. There are no known post-operative or surgical shoes that effectively remove weight from the rear foot while covering and protecting the heel portion of the foot.

It is therefore a primary object of the present invention to aid health care providers in treating patients with conditions of the rear foot that are made worse by weight bearing and to allow the patient to become ambulatory much earlier than they could in conventional shoes.

It is a further object of the invention to provide such a shoe designed to be used by patients who have either had surgery of the rear foot, trauma to the rear foot, or heel pain that is aggravated by weight bearing such as heel spur syndrome, plantar fascitis, calcinosis, Achilles tendonitis, or have skin lesions, ulcers or infections of the rear foot area where reduction of weight would enhance the healing process and allow the patient to be ambulatory.

SUMMARY OF THE INVENTION

The above and other objects of the invention which will become apparent hereinafter are achieved by the provision of a surgical shoe having a molded sole especially designed to prevent heel strike and to force weight on the initial impact of the foot with the ground to the area of the foot anterior to the medial tuberosity. Such is accomplished by constructing the outsole with a wedge shaped design with the thickest portion of the wedge being located under that part of the foot in the vicinity of the proximal portion of the arch and just in front of the heel. The sole then angles at about 3° forwardly and upwardly and extends anteriorly about 5 cm. The remainder of the sole is angled to a greater angle, with the final 2–3 inches of the sole being flat and of a normal thickness of about ½ inch to the toe. The upper surface of the outsole is designed to accommodate a metal or plastic shank to offer rigidity and additional support due to the higher pressure being concentrated on the smaller area of the sole in the area between the heel and the metatarsal-phalangeal joints. A plastic or metal shank may be 1 to 2 inches wide and would extend from a position above the thickest portion of the wedge distally to the area just proximal to the metatarsal-phalangeal joints. Preferably, a forward section of the insole would be of a medium density foam material and would extend from directly above the wedge to the toe end of the shoe. The heel section of the insole is preferably fabricated from either a soft conforming foam material or a gel material to provide a very soft pad cradling and protecting the traumatized heel. The upper of the shoe may be constructed of any type of material conventionally used for shoe uppers including fabric, leather or vinyl. The shoe may be an open or close toe shoe with either hook and loop strap or lace closures for the shoe flaps extending about the dorsal portion of the foot. Preferably, a strap fastens around the ankle area to serve as a heel lock and provide additional stability for the foot, with the heel captured between a heel counter to give stability along with a soft sponge or foam material liner to offer again a soft area for the heel within the Achilles triangle to prevent skin irritation.

DESCRIPTION OF THE PREFERRED EMBODIMENT

The post-operative medical shoe for supporting a traumatized patient's heel of this invention is an outgrowth of post-operative surgical shoes exemplified by U.S. Pat. No. 4,677,767 issued Jul. 7, 1987 to H. Darrel Darby and entitled "SHOCK ABSORBING SURGICAL SHOE" and U.S. Pat. No. 5,138,777 issued Aug. 18, 1992 to H. Darrel Darby and entitled "POST-OPERATIVE SHOES FOR USE AFTER FOREFOOT SURGERY".

Figure 1:
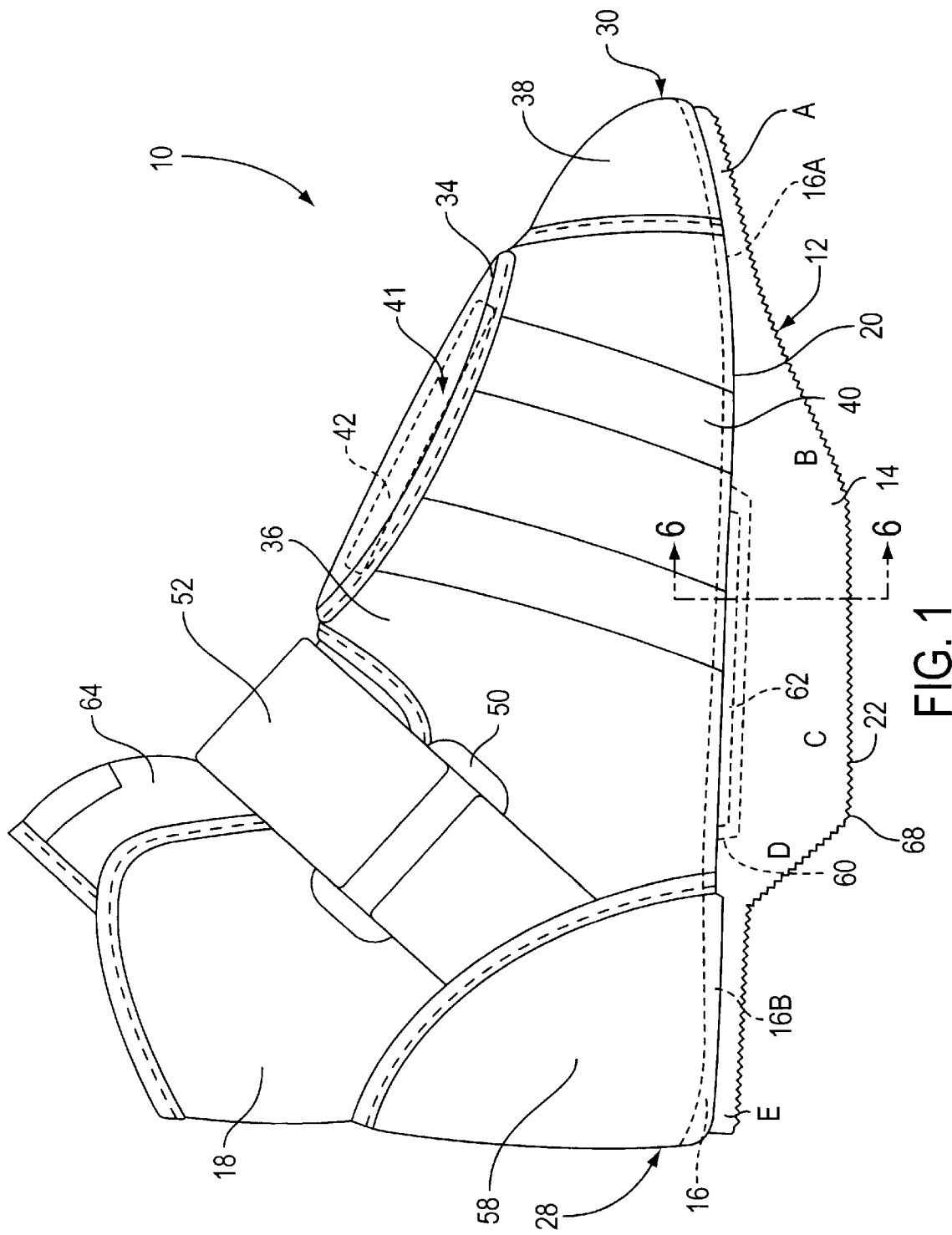
FIG. 1 is a side elevational view of a post-operative surgical shoe forming a preferred embodiment of the invention.

The post-operative surgical shoe of the present invention is indicated generally at 10, FIG. 1, and is formed principally of a sole assembly indicated generally at 12 and a shoe upper or upper assembly indicated at 18. The sole assembly 12 includes an outsole 14 underlying and adhesively bonded or otherwise coupled to a flat, thin insole 16. The outsole may be formed of a wear-resistant material such as rubber or a similar plastic material and preferably has a non-slip bottom surface with a tread or crepe pattern. The insole 16 is generally of the same thickness over the full extent of the insole, however, in the illustrated embodiment, the insole is formed of two distinct sections, a front or forward section 16A and rear or heel section 16B. The outsole 14 has a bottom surface 22 which is contoured and a flat top surface 20. That flat top surface 20 of the outsole is bonded to a flat bottom surface 24 of insole 16 via a thin layer of adhesive 26. The upper assembly 18 known conventionally as "the upper" is secured to the bottom surface of the insole 16 by conventional techniques, preferably by adhesive bonding. The upper with insole is then bonded to the upper surface of the outsole after the plastic or metal shank 62 is put into place, or to the outsole 14, or both. Preferably, the shape of the outsole 14 including the wedge configuration and the recess 60 for receiving the metal or plastic shank 62 are incorporated in the mold for molding the outsole 14. Similar to the construction of the upper in U.S. Pat. No. 5,138,777, which is incorporated herein by specific reference, the upper assembly has an outer wall of either nylon mesh or other suitable materials such as vinyl, leather, etc. and a lining of soft comfortable material such as foam which may be laminated between layers of fabric. A heel counter is incorporated within the upper as shown at 58, FIG. 1, which may be manufactured of suitable firm material or of molded plastic commonly used for that purpose. The upper, as does the insole 16 and outsole 14, extends the full length of the shoe from heel 28 to toe 30. The remainder of the upper is constructed in a conventional manner, with the closure of the dorsal aspect being accomplished by a left flap 34 and a right flap 36, closed using a hook type and loop type material strip assembly at 41, consisting of a pair of laterally extending, spaced loop material strips 40 fixed to the top surface of left flap 34 by a suitable adhesive, with the hook type side facing and underlying the right side flap 36 which carries on its bottom surface, as indicated in dotted lines at 42 (FIG. 1), an elongated right angle strip of hook type material 42. The hook and loop type elements engage to securely lock the flaps across the dorsal region, the hook and loop type material closure or system 41 being of the type sold under the registered trademark VELCRO®, for example. Preferably, the shoe upper 18 is completed by a tongue 64 which is fixed at one end in the area of toe box 38 which closes off the toe of the shoe above the insole 16 and extends beneath flaps 34, 36, with a free end of the tongue terminating above the portion of the trim strip 32 edging the heel 28 and sides of the shoe 10. While the shoe 10 is provided with a closed upper by the inclusion of a toe box 38, alternatively the shoe may be of the open toe type with either hook and loop type material closure system 41 or lace closures capturing the tongue 64. Alternatively, the tongue may be disposed of and the flap closure system be more akin to that of U.S. Pat. No. 5,138,777.

Figure 2:
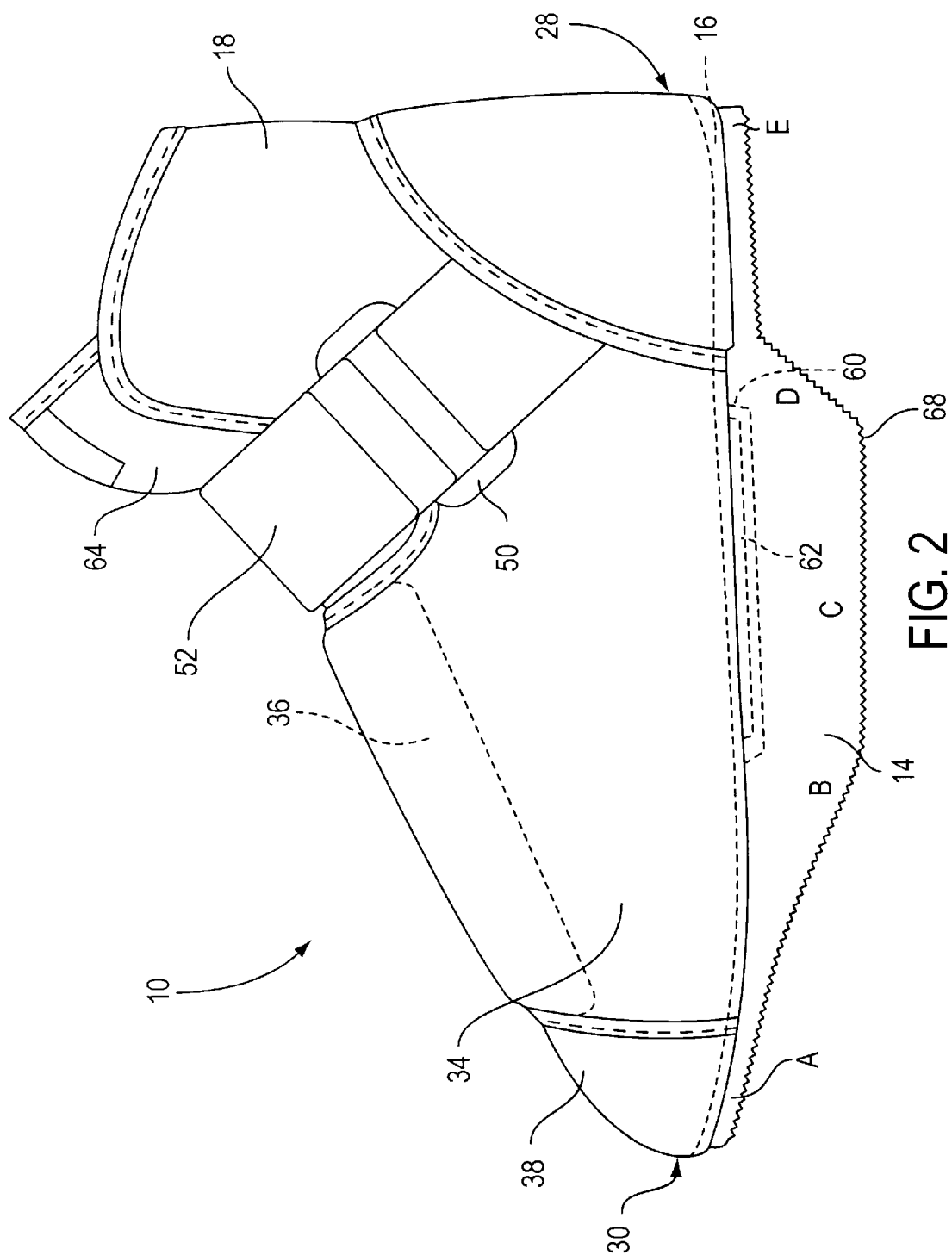
FIG. 2 is a side elevational view of the shoe of FIG. 1 to the opposite side thereof.

As may be seen in FIGS. 1 and 2, the ankle closure strap 52 loops between rings 50 to opposite sides of the shoe upper from right side 36 to the left side 34, with one end portion located below the ring 50, with the loop type material facing outwardly. The strap 52 is passed through the ring 50 to the juncture of the one end portion and the remainder of the strap, with that one end portion folded over so that the hook type material engages the loop type material of the adjacent portion of the strap, thereby restraining the one end of the strap on the corresponding ring 50. To complete the closure, the other, free end of the strap 52 is passed through the corresponding ring on the opposite flap 34 after insertion of thee foot and doubled back to engage the confronting hook like material adjacent that free end with the loop type fastening material. Such arrangement is described in detail in U.S. Pat. No. 5,138,777.

Figure 3:
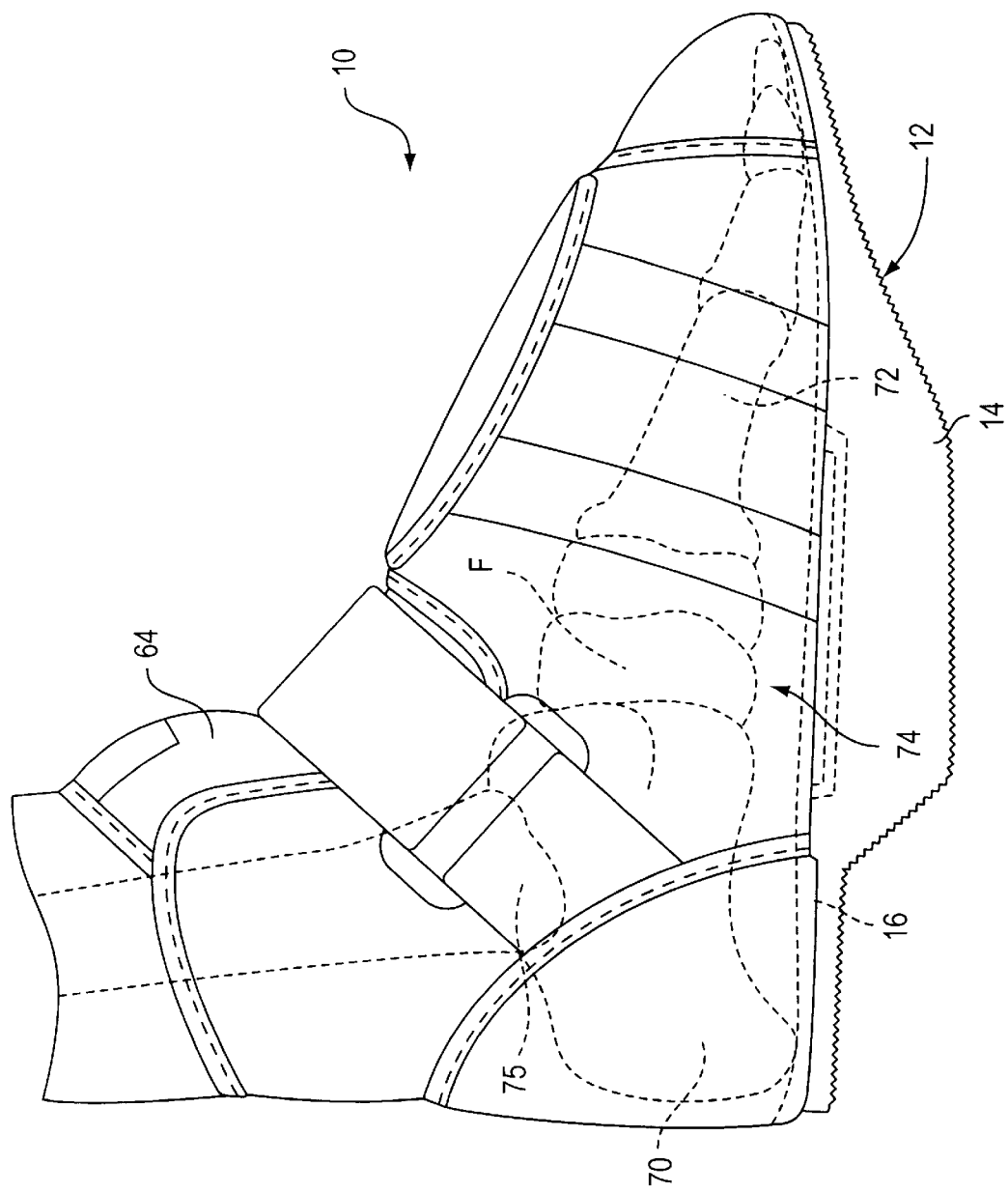
FIG. 3 is an enlarged, side elevational view with the bone structure of the heel portion of the foot being illustrated in dotted lines, with the shoe effecting both comfortable support for the traumatized heel of the foot, and the means for preventing heel strike during ambulation by the user.
Figure 4:
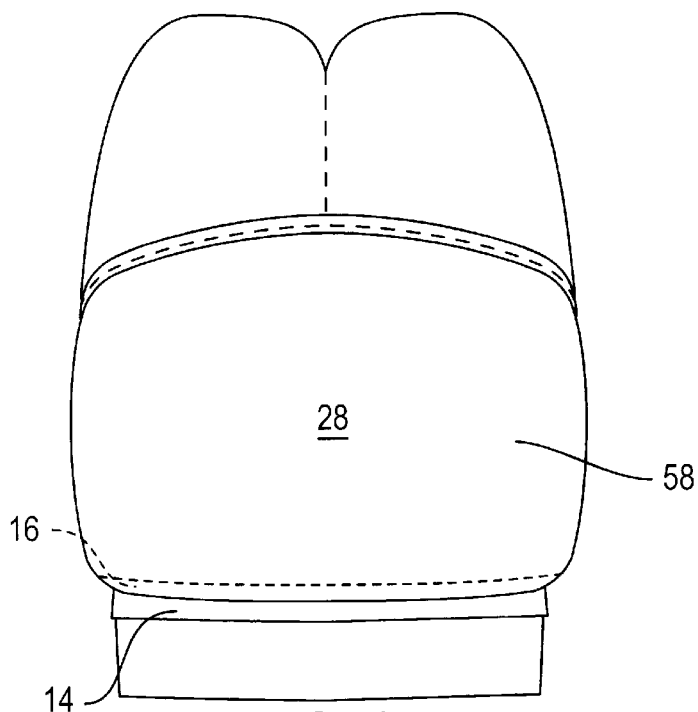
FIG. 4 is rear elevational view of the post-operative surgical shoe of FIG. 1.
Figure 5:
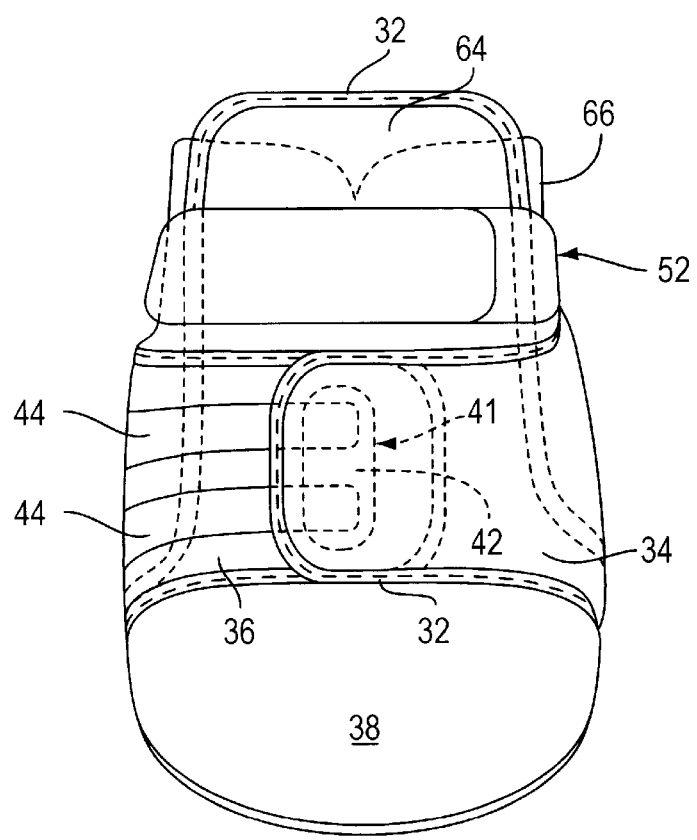
FIG. 5 is a front and top perspective view of the post-operative surgical shoe of FIG. 1 with portions shown in dotted lines which are hidden with the upper side flaps closed and the ankle strap.
Figure 6:
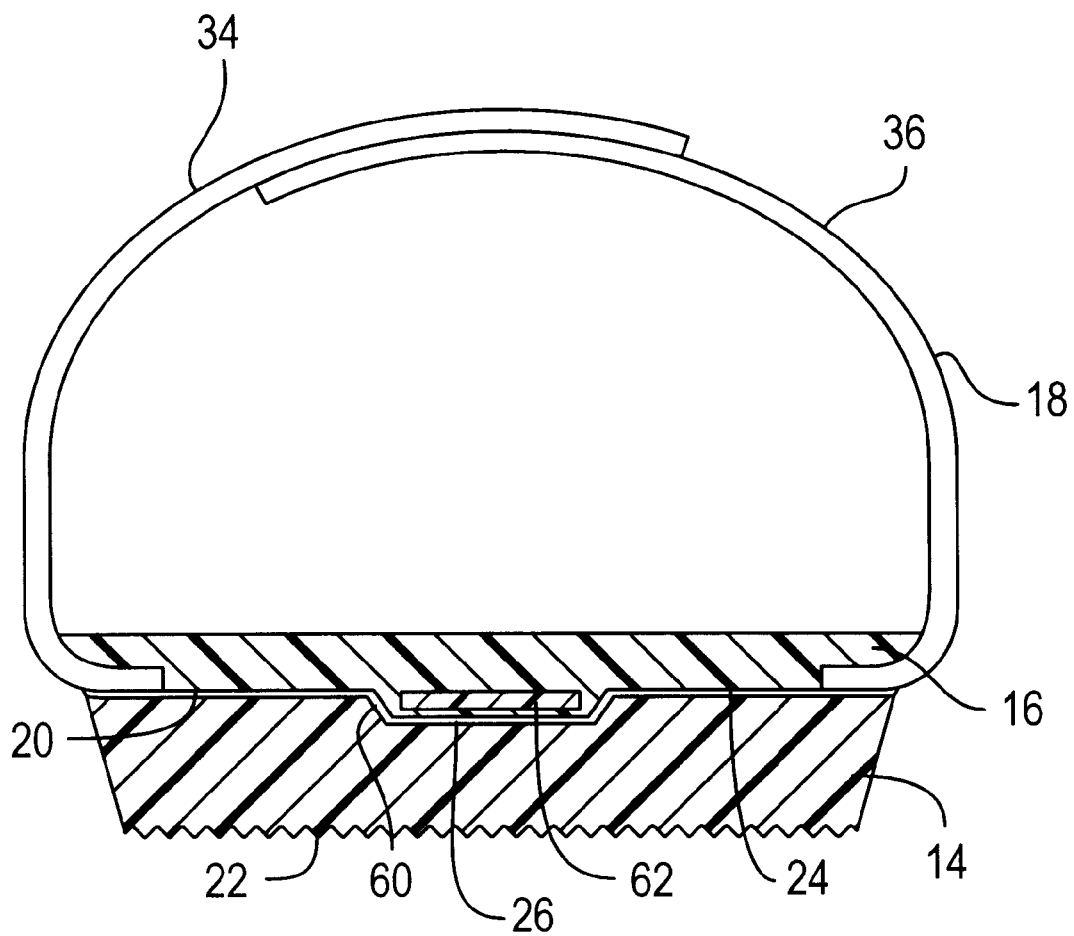
FIG. 6 is a cross-section of the shoe at mid metatarsal area taken about line 6—6 of FIG. 1.

A principal aspect of the surgical shoe 10 to avoid heel strike and to reduce the weight bearing capability of the shoe 10 from the heel area of the foot lies in the molded-in configuration of the outsole as illustrated best in FIG. 1. The vertical height or thickness of the outsole 14 varies considerably over the length of the same. From the toe 30 the outsole 14 is a short length toe portion A of a thickness which may be, for example, approximately ½ inch over a distance which is approximately one third the distance of the adjacent portion B which tapers obliquely rearwardly and downwardly and which underlies the metatarsals of the foot. A further section C of the outsole 14 extends a similar distance approximately three times that of section A, but at a shallow, downwardly and rearwardly oblique angle, terminating in the vicinity of the proximal margin of the arch 74, FIG. 3. The foot F is illustrated in FIG. 3 by dotted lines in terms of the bone structure thereof overlying the maximum thickness point of the outsole defined by transverse rocker edge 68, FIG. 1. Thereafter, the vertical thickness of the insole section D diminishes sharply over a distance generally 1½ times the length of the toe portion A. Heel section E is of a thickness which is on the order of the ½ inch thickness of the toe portion A of the outsole 14. The sharp upwardly and rearwardly oblique portion D functions with the heel portion E of the outsole 14 to significantly reduce the weight bearing capability of the shoe 10 at the heel area of the shoe. The configuration, therefore, of the molded outsole 14 acts in conjunction with the soft foam or gel section 16B of the insole and along with the foam lined interior of the shoe upper 18 in the heel 28 region to provide comfort to the user while alleviating heel strike during ambulation and ensuring that it is the portion forward of the rocker edge 68 of the outsole that firmly yet comfortably supports the weight of the user during ambulation. The metal or plastic shank 62 may be of a width on the order of the lateral width of the outsole 14 within a recess 60 of which it is mounted and between the insole 16 and outsole 14 as shown in FIG. 6, or may be limited to one to two inches in width, with its rear edge terminating in the vicinity of the maximum thickness of the insole 14, as per FIG. 1.

The shoe 10 therefore is purposely defined to significantly remove the weight from the rear foot, while covering and protecting the heel portion of the foot. In FIG. 3, the heel bone 70 is shown as being significantly rearwardly of the ankle bone 75, with the abrupt and significant thinning of the outsole 14 underneath the heel bone ensuring such reduction in weight bearing capability of the shoe, while providing significant weight bearing capacity of the shoe in the vicinity of arch 74, and that of the mid metatarsals indicated at 72 in FIG. 3.

It will be understood that while a preferred embodiment of the invention has been shown and described, changes and additions may be made therein and thereto without departing from the spirit of the invention. Reference should, accordingly, be had to the appended claims in determining the scope of the invention.

What is claimed is:

1. In a post-operative surgical shoe for supporting a post-operative or otherwise traumatized patient's heel, said shoe comprising:

an upper assembly secured to a sole assembly, said upper assembly adapted to surround the heel sides and dorsal portions of a foot;

a forward portion of said upper assembly being divided into left and right side flaps adapted to cover the dorsal region of said foot;

means detachably interconnecting outer face portions of said left and right flaps;

said sole assembly comprising at least an insole conforming generally to the plantar aspect of the foot and an outsole having a flat top surface and being integrated to the bottom surface of said insole, the improvement wherein;

said outsole is of generally wedge shape in side elevation tapering generally towards the toe of the shoe and having a thickest portion of a wedge located under a part of the foot just in front of the heel, defining a rocker edge and an integral, substantially thinner portion extending rearwardly along said flat top surface from said thickest portion and underlying the heel of the foot, elevated from the bottom surface of said thickest portion of said outsole and thereby defining a rearwardly extending recess underlying the heel of the foot, raised above said rocker edge to thereby shift initial ground contact to said rocker edge in front of the heel and proximal to the arch to prevent heel strike and to avoid weight bearing directly under the heel during both ambulation and standing;

and wherein said insole further comprises a front section overlying said outsole from said thickest portion of said forwardly tapering outsole to said toe end of said shoe of a medium impact material, and a rear section underlying the heel of the foot of a soft conforming material to cradle and protect the heel.

2. The post-operative surgical shoe as claimed in claim 1, wherein said thickest portion of said wedge shaped outsole generally flat bottom surface lies under the arch of the foot towards said toe end of the shoe leading to an upwardly and forwardly oblique bottom surface terminating at a metatarsal joint area and a further generally flat bottom surface underlying the toe of the foot.

3. The post-operative surgical shoe as claimed in claim 1, further comprising a relatively stiff, thin, flat shank interposed between said insole and said outsole and extending from said thickest portion of said outsole to an area just proximal to the metatarsal-phalangeal joint region of said foot.

4. The post-operative surgical shoe as claimed in claim 3, wherein said stiff, thin, flat shank is fitted within a recess within the top surface of said outsole.

5. The post-operative surgical shoe as claimed in claim 4, wherein the width of said stiff, thin, flat shank is less than the width of said outsole.

6. The post-operative surgical shoe as claimed in claim 5, wherein said stiff, thin, flat shank is of a width of one to two inches.

7. The post-operative surgical shoe as claimed in claim 3, wherein said shank is of one material from the group consisting of a metal and plastic.

8. The post-operative surgical shoe as claimed in claim 1, wherein said frontal section of said insole is of a medium density foam material.

9. The post-operative surgical shoe as claimed in claim 8, wherein said insole rear section is a gel.

10. The post-operative surgical shoe as claimed in claim 1, wherein said insole rear section is of a soft foam material.

* * * * *